United States Patent [19]

Gashinsky et al.

[11] Patent Number: 4,939,150

[45] Date of Patent: Jul. 3, 1990

[54] METHOD FOR PREPARING DENSE NUTRIENT MEDIUM FOR CULTURING MICROORGANISMS

[76] Inventors: Vladimir V. Gashinsky, ulitsa Repina, 7/13, kv. 11; Vladimir P. Shirobokov, ulitsa Malyshko, 3, kv. 538; Nikolai N. Marchenko, bulvar I. Lepse, 49, kv. 33; Valery G. Voitsekhovsky, ulitsa Betkhovena, 18; Tatyana I. Krainjukova, ulitsa Zakrevskogo, 11, kv. 120, all of Kiev; Vladimir V. Onischenko, ulitsa Novaya, 6, kv. 140, Kievskaya oblast, Fastov, all of U.S.S.R.

[21] Appl. No.: 283,950

[22] PCT Filed: Jan. 7, 1988

[86] PCT No.: PCT/SU88/00006

§ 371 Date: Sep. 30, 1988

§ 102(e) Date: Sep. 30, 1988

[87] PCT Pub. No.: WO88/05794

PCT Pub. Date: Aug. 11, 1988

[30] Foreign Application Priority Data

Jan. 30, 1987 [SU] U.S.S.R. ............................. 4182247
Jun. 25, 1987 [SU] U.S.S.R. ............................. 4278310

[51] Int. Cl.$^5$ ............................................. C12N 1/20

[52] U.S. Cl. .................................. 435/253.6; 524/377; 526/306; 526/307.2

[58] Field of Search ...................... 435/253.6; 524/377; 526/306, 307.2

[56] References Cited

U.S. PATENT DOCUMENTS 3,061,595 10/1962 Dorion et al. ........................ 526/306

FOREIGN PATENT DOCUMENTS

| 3106456 | 10/1982 | Fed. Rep. of Germany. | |
| 658169 | 4/1979 | U.S.S.R. | 435/260 |
| 659619 | 4/1979 | U.S.S.R. | 435/253.6 |
| 977466 | 11/1982 | U.S.S.R. | |
| 1213069 | 2/1986 | U.S.S.R. | |
| WO8101290 | 5/1981 | World Int. Prop. O. | 526/306 |

Primary Examiner—Robert A. Wax
Attorney, Agent, or Firm—Burgess, Ryan & Wayne

[57] ABSTRACT

A method for preparing a dense nutrient medium for culturing microorganisms comprises copolymerization of acrylamide, N,N'-methylenebisacrylamide and a branched polyacrylamide with the mean molecular mass of $7.2 \times 10^4$ at a mass ratio therebetween of 7.0–15:0.11–0.21:0.028–0.11 respectively and of an initiator in a physiological solution till the formation of a gel which is then washed and impregnated with a nutrient substrate.

3 Claims, No Drawings

METHOD FOR PREPARING DENSE NUTRIENT MEDIUM FOR CULTURING MICROORGANISMS

FIELD OF THE ART

The present invention relates to a method for preparing a dense nutrient medium based on a polyacrylamide gel for culturing microorganisms.

STATE OF THE ART

Known in the art is a method for preparing a dense nutrient medium for culturing microorganisms by way of copolymerization of acrylamide and N,N'-methylenebisacrylamide at a mass ratio thereof equal to 15–20:0.019–0.132 in the presence of an initiator in a physiological solution till the formation of a gel, its washing and swelling in a physiological solution for 16–20 hrs at a temperature within the range of from 50° to 60° C., followed by impregnation with a nutrient substrate.

This dense nutrient medium has a density approaching that of agar-agar media, it is elastic and transparent. It also ensures a good sliding of a bacteriological loop upon inoculation and removal of microorganisms without damaging its surface owing to a long-time operation of swelling (16–20 hrs), thus substantially extending the duration of the entire process.

Known in the art is a method for preparing a nutrient medium for culturing microorganisms comprising copolymerization of acrylamide and N,N'-methylenebisacrylamide at a mass ratio thereof equal to 0.5–40:2.5–12.0 in the presence of an initiator in a physiological solution. The resulting polyacrylamide gel is subjected to washing and impregnation with a nutrient substrate (SU, A, 977466). This dense nutrient medium has a greater sensitivity to damages during imprenation, sterilization and inoculation of microorganisms. The removal of individual species of microorganisms from the surface of such medium by means of a bacteriological loop is rather difficult.

In the above-discussed methods the process of copolymerization is effected in special moulding apparatus without access of air to exclude the formation of a rough surface on the produced polyacrylamide gel hindering its use for the preparation of a nutrient medium. This process, therefore, has but a limited application in the mass-scale preparation of nutrient media, for example in Petri dishes and in other laboratory ware.

DISCLOSURE OF THE INVENTION

The present invention is directed to the provision of a method for preparing a dense nutrient medium for culturing microorganisms by way of using, during copolymerization, a structurization agent which would impart, to the nutrient medium, the properties similar to those of agar-agar media while ensuring a good effect of sliding of a bacteriological loop in the process of inoculation of microorganisms.

This problem is solved by the provision of a method for preparing a dense nutrient medium for culturing microorganisms which comprises copolymerization of acrylamide and N,N'-methylenebisacrylamide in the presence of an initiator in a physiological solution till the formation of a gel, washing and impregnation thereof with a nutrient substrate, wherein, according to the present invention, the copolymerization of acrylamide and N,N'-methylenebisacrylamide is carried out in the presence of a branched polyacrylamide with a mean molecular mass of $7.2 \times 10^4$ at a mass ratio thereof equal to 7–15.0:0.11–0.21:0.028–0.11 respectively.

The method, according to the present invention, provides for a good quality of the nutrient medium at a simplified process of its manufacture. The process of copolymerization, owing to the use of the structurization agent, is readily implementable in the air atmosphere without the necessity of using special equipment.

To accelerate the reaction of copolymerization, it is advisable to use an aqueous solution of the above-mentioned branched polyacrylamide. It is desirable to use, for the impregnation of the polyacrylamide gel, a nutrient substrate containing polyethylene oxide in an amount of 0.02 to 0.2 g/l. This contributes to the formation of such a superficial monolayer on the surface of the medium which ensures a clearly pronounced effect of sliding of a bacteriological loop in inoculation of microorganisms.

THE BEST WAY OF CARRYING THE INVENTION INTO EFFECT

The dense nutrient medium for culturing microorganisms, according to the present invention, is prepared in the following manner.

A reaction mixture is prepared which contains solutions of the starting monomers, a branched polyacrylamide with the molecular mass of $7.2 \times 10^4$ and initiators in a pgysiological solution. It is also possible to use an aqueous solution of the above-specified branched polyacrylamide. The ratio of acrylamide and the branched polyacrylamide in the reaction mixture is 7.0–1.5:0.0-28–0.11 respectively.

As the physiological solution use is made of a 0.5% or a 0.9% solution of sodium chloride, a 5% aqueous solution of glucose, the Ringer-Lock solution, Hanks solution, Earl solution and the like. The copolymerization is conducted in the air in a Petri dish or in other vessels made from different materials.

The process of copolymerization in the presence of a branched polyacrylamide employed in the above-specified proportions enables the production of a polyacrylamide gel with a density close to that of the agar base. Furthermore, the use of a branched polyacrylamide results in an additional structurization of the polyacrylamide gel, thus enabling the formation of an even smooth surface thereof upon polymerization in Petri dishes in the air. Previously such an effect could be obtained only upon polymerization in special apparatus without access of air and with the use of inert gases. In the method for preparing nutrient media, according to the present invention, the stage of the gel swelling for 16–20 hours is excluded.

All the above-mentioned advantages substantially simplify the process for the preparation of a nutrient medium.

After washing, the polyacrylamide gel is subjected to sterilization by way of a thermal, radiation or chemical treatment. The impregnation of the above-mentioned gel with substrates for nutrition of microorganisms can be effected both before and after sterilization. It is advisable to use nutrient substrates containing polyethylene oxide with a molecular mass of from 500,000 onwards in an amount of from 0.02 to 0.2.

The substrate composition is defined by the needs of particular groups or species of microorganisms and cells.

For the determination of the quality of nutrient media, as well as for the study of biological properties of microorganisms, generally accepted investigation procedures are employed.

Specific examples illustrating some particular embodiments of the method, according to the present invention, are given hereinbelow.

EXAMPLE 1

For the production of a gel five solutions A, B, C, D and E are prepared following the procedure specified hereinbelow (the component amounts are given per 100 ml of the solution).

1. Preparation of solution A 0.5 ml of N,N,N',N'-tetramethylenediamine (TEMED) is dissolved in 99.5 ml of a physiological solution. 2. Preparation of solution B 0.735 g of N,N'-methylenebisacrylamide (MBA) is dissolved in 50 ml of a physiological solution, heated to the temperature of 60° C., added with 24.5 g of acrylamide (AA) and stirred till a complete dissolution. The resulting solution is filtered and brought to the volume of 100 ml by means of a physiological solution.

3. Preparation of solution C 0.2 g of ammonium persulphate (AP) is dissolved in 50 ml of a physiological solution and brought to the volume of 100 ml.

4. Preparation of solution D 10.0 g of a branched polyacrylamide (BPA) with the molecular mass of $7.2 \times 10^4$ are dissolved in 50 ml of a physiological solution at a temperature of 50°–60° C. The volume of the solution is brought to 100 ml.

5. Preparation of solution E 0.5 ml of solution D is mixed with 99.5 ml of solution C and thoroughly intermixed.

The reaction mixture is prepared from the solutions employed in the following ratio: A:B:E:=1:2:4 respectively which corresponds to the mass ratio of acrylamide to N,N'-metylenebisacrylamide and to the branched polyacrlamide equal to 7.0:0.21:0.028. The mixture is poured into Petri dishes and allowed to stay in the air. The copolymerization occurs for 10–15 mn till the formation of a gel which is then washed with a physiological solution for one hour.

A dense nutrient medium is prepared by impregnation of the resulting gel with the Hottingen tryptic digestion broth.

The nutrient medium is inoculated with *Staphylococcus aureus* and incubated at the temperature of 37° C. for 24 hrs. The dense nutrient medium has good adhesion properties, density, transparency and elasticity, it has a smooth surface ensuring the effect of sliding of a bacteriological loop upon inoculation of the microorganisms without damaging the surface. The grown microorganisms demonstrate characteristic cultural and morphological features.

EXAMPLE 2

For the preparation of a polyacrylamide gel solutions A, B, C and D are used likewise in the foregoing Example 1.

The reaction mixture is prepared from the solutions at the ratios of A:B:E=1:2:4 which corresponds to the mass ratio of acrylamide, N,N'-,ethylenebisacrylamide and the branched polyacrylamide of 7.0:0.21:0.057. The mixture is poured into Petri dishes and allowed for polymerization in the air. The copolymerization occurs for 5–10 minutes until a gel is formed which is then washed with a physiological solution for one hour.

The resulting gel is impregnated with a meat-peptone broth for 3 hours at the temperature of 56° C., followed by sterilization for 30 minutes.

The nutrient medium is inoculated with colibacillus and incubated at the temperature of 37° C. for 24 hours. The grown microorganisms reveal cultural and morphological features characteristic therefor. The dense nutrient medium has good adhesion properties, density, transparency, elasticity; it has a smooth surface ensuring the effect of sliding for a bacteriological loop upon inoculation of the microorganisms without damaging the surface.

EXAMPLE 3

For the preparation of a polyacrylamide gel three solutions A, B and C are obtained according to the following procedure.

1. Preparation of solution A 0.23 ml of N,N,N',N'-tetramethylethylenediamine is dissolved in 50 ml of a physiological solution and brought to the volume of 100 ml.

2. Preparation of solution B 0.4 g of N,N'-methylenebisacrylamide is dissolved in 50 ml of a physiological solution, heated to the temperature of 60° C., added with 53 g of acrylamide and stirred till a complete dissolution. The resulting solution is filtered, brought to the volume of 100 ml.

3. Preparation of solutions C and D

The solutions C and D are prepared in a manner similar to that described in Example 1 hereinbefore.

4. Preparation of solution E 2 ml of solution D are introduced into 98 ml of solution C and thoroughly intermixed.

A reaction mixture is produced from the resulting prepared solutions. To this end, the solutions are mixed in the ratio of A:B:E=1:2:4 which corresponds to the mass ratio of acrylamide, N,N'-methyleneacrylamide and the branched polyacrylamide of 15.0:0.11:0.11 and poured into Petri dishes. The copolymerization is conducted in the air for 10–15 minutes till a gel is formed. The resulting gel is washed with physiological solution for one hour. The gel is then subjected to impregnation with a meat-peptone broth for 3 hours at a temperature of 50°–60° C. and a spore culture is inoculated after sterilization.

The resulting dense nitrient medium has good adhesion properties, elasticity, density, transparency; it also features a smooth surface, a clearly pronounced effect of sliding of a bacteriological loop upon inoculation of microoganisms. The grown culture is typical.

EXAMPLE 4

A polyacrylamide gel is produced in a manner similar to that described in Example 1 hereinbefore, while the impregnation is effected in the Hottinger tryptic digestion broth containing 0.2 g/l of polyethyleneoxide for 3 hours at the temperature of 56° C. The impregnated gel is sterilized for 30 minutes and inoculated with Staphylococcus aureus.

The resulting dense nutrient medium exhibits good adhesion properties, elasticity, density, transparency and a clearly pronounced effect of sliding upon inoculatoin of the microorganisms by means of a bacteriological loop without damaging the culture surface. The grown culture is typical.

EXAMPLE 5

A polyacrylamide gel is produced as in Example 3 hereinbefore, while the impregnation is effected by means of a meat-peptone broth containing 0.02 g/l of polyethyleneoxide for 3 hours at the temperature of 56° C., followed by sterilization for 30 minutes.

The resulting dense nutrient medium features good adhesion properties, elasticity, density, transparency; it also has a clearly pronounced aliding effect upon incoulation of the microorganisms by means of a bacteriological loop without damaging the culture surface thereby.

As the test-microbe colicacillus is used.

The culture grows in the form of typical colonies.

INDUSTRIAL APPLICABILITY

The dense nutient medium, according to the present invention, is useful in medicine and biotechnology.

We claim:

1. A method for preparing a dense nutrient medium for culturing micoorganisms comprising copolymerization of acrylamide and N,N'-methylenebisacrylamide in the presence of an initiator in a physiological solution till the formation of a gel, washing and impregnation thereof with a nutrient substrate, characterized in that said copolymerization of acrylamide and N,N'-methylenebisacrylamide is conducted in the presence of a branched polyacrylamide with the mean molecular mass of $7.2 \times 10^4$ at a mass ratio thereof equal to 7.0–15:0.11:–0.21:0.028–0.11 respectively.

2. A method according to claim 1, characterized in that an aqueous solution of said polyacrylamide is used.

3. A method according to claims 1 and 2, characterized in that said impregnation of said gel is effected by means of a nutrient substrate containing polyethyleneoxide in an amount of from 0.02 to 0.2 g/l.

* * * * *